United States Patent [19]

Yamaguchi

[11] Patent Number: 5,517,126
[45] Date of Patent: May 14, 1996

[54] PROBE APPARATUS

[75] Inventor: Masao Yamaguchi, Tokyo, Japan

[73] Assignee: Tokyo Electron Limited, Tokyo, Japan

[21] Appl. No.: 92,790

[22] Filed: Jul. 19, 1993

[30] Foreign Application Priority Data

Mar. 18, 1993 [JP] Japan .................................. 5-085661

[51] Int. Cl.⁶ ................................................. G01R 31/02
[52] U.S. Cl. ........................ 324/758; 324/754; 324/760
[58] Field of Search ........................... 324/158 F, 158 P, 324/72.5, 754, 757, 758, 760; 439/482

[56] References Cited

U.S. PATENT DOCUMENTS

| | | | |
|---|---|---|---|
| 4,649,339 | 3/1987 | Grangroth | 324/158 F |
| 5,124,639 | 6/1992 | Carlin | 324/158 P |
| 5,186,238 | 2/1993 | del Puerto | 165/80.4 |
| 5,254,939 | 10/1993 | Anderson | 324/158 P |
| 5,325,052 | 6/1994 | Yamashita | 324/754 |

FOREIGN PATENT DOCUMENTS

| | | |
|---|---|---|
| 59-3537 | 1/1984 | Japan . |
| 6159849 | 8/1984 | Japan . |
| 62-98234 | 6/1987 | Japan . |
| 1-235344 | 9/1989 | Japan . |
| 3-224246 | 10/1991 | Japan . |

*Primary Examiner*—Ernest F. Karlsen
*Assistant Examiner*—Russell M. Kobert
*Attorney, Agent, or Firm*—Oblon, Spivak, McClelland, Maier & Neustadt

[57] ABSTRACT

A probe apparatus for measuring electrical characteristics of an object to be tested by putting a plurality of probes in electrical contact with the object comprises an apparatus body, a probe card having a plurality of probes, and a probe card holder for holding the probe card at a measurement position facing the object. A memory device for memorizing data for measuring the object is provided on the probe card holder.

11 Claims, 7 Drawing Sheets

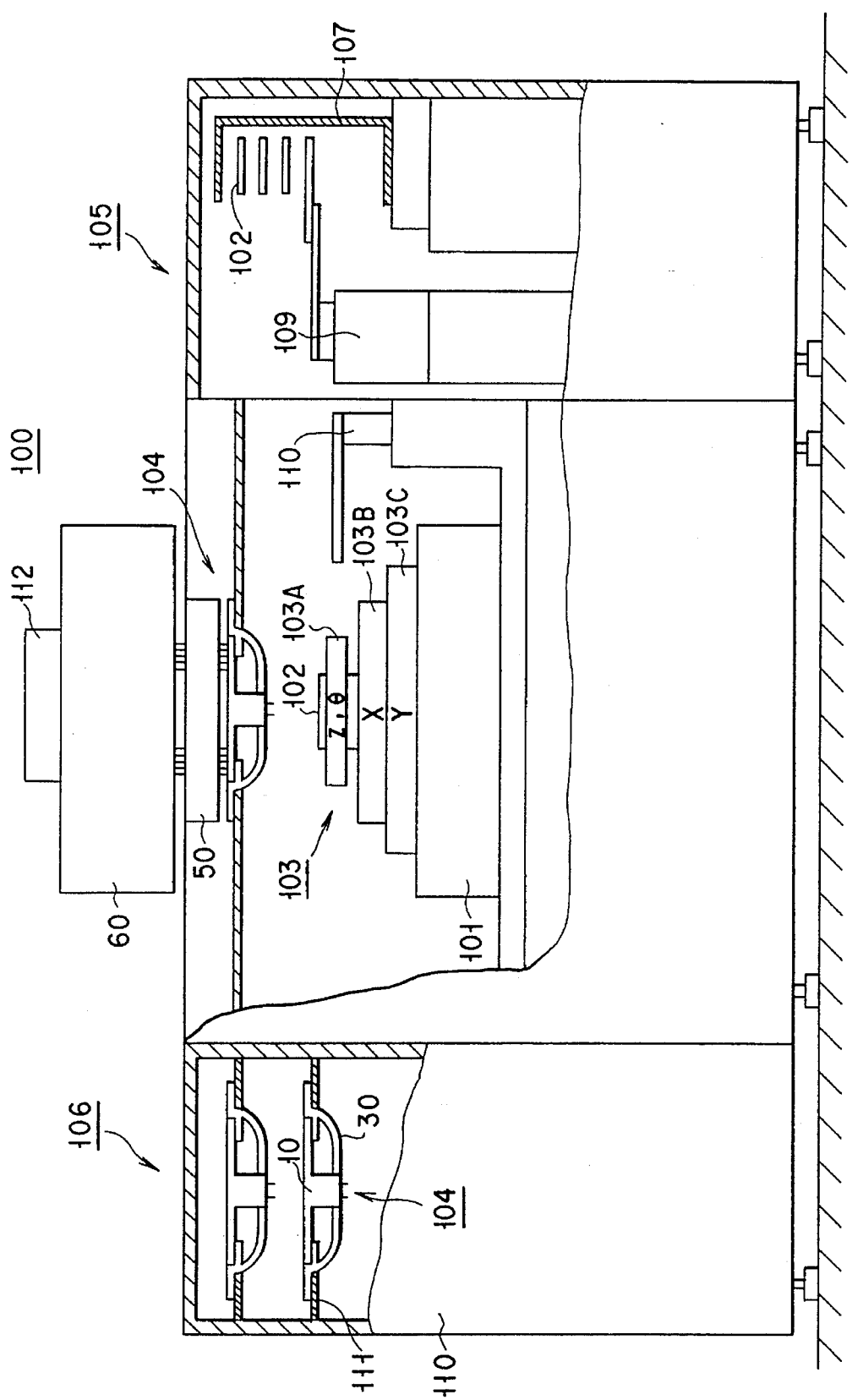
F I G. 1

PROBE APPARATUS

BACKGROUND OF THE INVENTION

1. Field of the Invention

The present invention relates to a probe apparatus for measuring electrical characteristics of an object such as a semiconductor wafer on which a plurality of semiconductor devices are formed or a glass substrate on which pixel drive circuits constituting a liquid crystal device are formed, and more particularly to a probe apparatus characterized by a probe card holder for holding a probe card.

2. Description of the Related Art

As is well known, a great number of semiconductor devices are formed on a semiconductor wafer by employing precise photographic transfer techniques, and the wafer is cut to separate individual semiconductor devices. In a conventional process of manufacturing such semiconductor devices, a probe apparatus is used to test and evaluate electrical characteristics of semi-finished semiconductor devices as formed on the semiconductor wafer. Only a semiconductor wafer, the condition of which has been judged to be good, is subjected to a subsequent step such as packaging, thereby enhancing productivity.

The probe apparatus includes a wafer table which is movable in X-, Y-, Z- and θ-directions. A probe card having many probes corresponding to electrode pads of semiconductor devices is fixed above the wafer table by means of a suitable probe holder. When measurement is performed, an object such as a semiconductor wafer is placed and fixed on the wafer table, and the wafer table is moved such that the probe needles are put in contact with the electrodes of the semiconductor devices. The semiconductor devices are tested via the probes.

In a probe test, it is desirable that data items peculiar to probe cards, such as type numbers, the number of times of use, etc., be managed on a card-by-card basis. Thus, it has been proposed to provide a memory device for memorizing such data above the probe card (Published Unexamined Japanese Utility Model Application (PUJUMA No. 59-3537).

However, since the integration density on the semiconductor wafer has been increased, as mentioned above, it is necessary to arrange 1000 to 3000 probes on a probe card constituted by a printed circuit board and to provide wiring areas associated with the probes and land areas for contact with a tester. It is difficult to find a room for providing the above-mentioned memory device on each probe card having 1000 to 3000 probes and electrodes for providing electric lead wires of these probes. Even if it is possible to provide the memory device on the probe card, the memory device may be affected by noise or crosstalk from the probe card, and the exact operation of the memory device cannot be ensured. Furthermore, measurement signals which are processed at high speed via the probes may be adversely affected. Thus, it is desired to provide the memory device in such a position as to be movable with the probe card, without such adverse affection.

On the other hand, according to modern art relating to the probe apparatus of the above type, the contact between each probe on the probe card and the tester is effected by a pogo contact technique wherein spring-urged contact pins (pogo pins) are put in pressure contact with electrode land areas connected by electric lead wires. As regards this technique, for example, in the case where 100 probe needles are put in contact with the tester during tests, if a force of about 10 g is exerted on each probe, a force of about 1 kg is exerted on the entire probe card.

In particular, with higher integration of semiconductor devices in, e.g. a CPU of a supercomputer, the number of probes necessary for testing one chip increases more and more. Recently, in the field of semiconductor manufacture, there is a demand for the above-mentioned probe card having 1000 to 3000 probes, and in some cases such many probe needles are provided in a very small region of, e.g. 2 cm×2 cm. In such a case, a force of 10 kg to 30 kg is applied to the entire probe card. When a force of a predetermined value or more is exerted on a probe card, the probe card is deformed in a Z-direction in accordance with the exerted force. If such a great force is exerted, the degree of deformation or strain is very high and the probes cannot be put in contact with the object with uniform pressure and uniform parallelism. Consequently, exact tests are not performed. To solve this problem, some techniques have been proposed to increase the strain-resistant properties of the probe card itself, but there is a limit to such techniques and there is a demand for advent of novel techniques.

In addition, there has recently been put into practice a method of measuring electrical characteristics of a semiconductor wafer at high temperatures by heating the wafer from room temperature up to about 150° C. by means of a table on which the wafer is placed. In the case of such high-temperature measurement, a probe card holder formed of a metallic member such as stainless steel or aluminum, which tends to be more thermally deformable than the probe card, is considerably deformed, and the probes are not put in contact with the object with uniform pressure and uniform parallelism. Consequently, exact tests cannot be performed. Therefore, it is desired to enhance the strain-resistant characteristics of the probe card holder for the purpose of high-temperature measurement.

SUMMARY OF THE INVENTION

The present invention has been made in consideration of the above circumstances, and an object of the invention is to provide a probe apparatus wherein even if each probe card has no physical space for situating a memory device for memorizing data peculiar to the probe card, such a memory device can be mounted, and no adverse affection occurs between the memory device and signal lines of the probe card.

Another object of the invention is to provide a probe apparatus having a novel, improved probe card holder, with which even when a force is applied to the probe card at the time of measurement, the strength of the probe card can be reinformed and a Z-directional strain of the probe card can be prevented.

Still another object of the invention is to provide a probe apparatus wherein even when an object is tested at high temperatures or low temperatures, a strain of the probe card holder itself can be corrected and exact measurement can be performed.

Still another object of the invention is to provide a probe apparatus wherein exact and good contact can be effected when a tester is put in electrical contact with a probe card at the time of measurement.

According to a first aspect of the invention, there is provided a probe apparatus for measuring electrical characteristics of an object to be tested by putting a plurality of probes in electrical contact with the object, said apparatus comprising: an apparatus body; probe card means having a plurality of probes; a probe card holder for holding said probe card means at a measurement position facing said object; and memory means, provided on said probe card holder, for memorizing data for measuring the object.

According to a second aspect of the invention, there is provided a probe apparatus for measuring electrical characteristics of an object to be tested by putting a plurality of probes in electrical contact with the object, said apparatus comprising: an apparatus body; probe card means having a plurality of probes, a base plate for supporting said probes, and a guide member for guiding said probes; and a probe card holder for holding said probe card means at a measurement position facing said object within the apparatus body, wherein said probe card holder includes a first portion for supporting an outer peripheral portion of a lower surface of the base plate of said probe card means and a second portion engaged with said guide member of the probe card means.

According to a third aspect of the invention, there is provided a probe apparatus for measuring electrical characteristics of an object to be tested by putting a plurality of probes in electrical contact with the object, said apparatus comprising: an apparatus body; probe card means having a plurality of probes; and a probe card holder for holding said probe card means at a measurement position facing said object within the apparatus body, wherein said probe card holder is provided with holes or grooves extending in the circumferential direction thereof such that a thermal stress applied to said probe card holder at the time of measurement is reduced.

According to a fourth aspect of the invention, there is provided a probe apparatus for measuring electrical characteristics of an object to be tested by putting a plurality of probes in electrical contact with the object, said apparatus comprising: an apparatus body; probe card means having a plurality of probes; and a probe card holder for holding said probe card means at a measurement position facing said object within the apparatus body, wherein said probe card holder comprises a combination of materials having different thermal expansion coefficients such that thermal deformation at the time of measurement is canceled.

According to a fifth aspect of the invention, there is provided a probe apparatus for measuring electrical characteristics of an object to be tested by putting a plurality of probes in electrical contact with the object, said apparatus comprising: an apparatus body; probe card means having a plurality of probes; a probe card holder for holding said probe card means at a measurement position facing said object within the apparatus body; first contact means for transmitting test data obtained through measurement by said probe card means to a tester; memory means, provided on a surface portion of said probe card holder, for memorizing data for measuring the object by using said probe card means; memory means, provided on said probe card holder, for memorizing data for measuring the object by using said probe card means; and second contact means for reading/writing data from/in said memory means, wherein at the time of measurement, said probe card means is held between said first contact means and said probe card holder, and said memory means is held between said second contact means and said probe card holder.

According to a sixth aspect of the invention, there is provided a probe apparatus for measuring electrical characteristics of an object to be tested by putting a plurality of probes in electrical contact with the object, said apparatus comprising: an apparatus body having a supporting portion; probe card means having a plurality of probes, a base plate for supporting said probes, and a guide member for guiding said probes; and a probe card holder, supported by said supporting portion within said apparatus body, for holding said probe card means at a measurement position facing said object, wherein said probe card holder includes a first portion for supporting an outer peripheral portion of a lower surface of the base plate of said probe card means and a second portion engaged with said guide member of the probe card means, and the parallelism of a first engaging surface between said supporting portion of said apparatus body and said first portion and the parallelism of a second engaging surface between said guide member and said second portion are adjusted.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 shows schematically the structure of a probe apparatus according to an embodiment of the present invention;

DETAILED DESCRIPTION OF THE PREFERRED EMBODIMENTS

Figure 2:
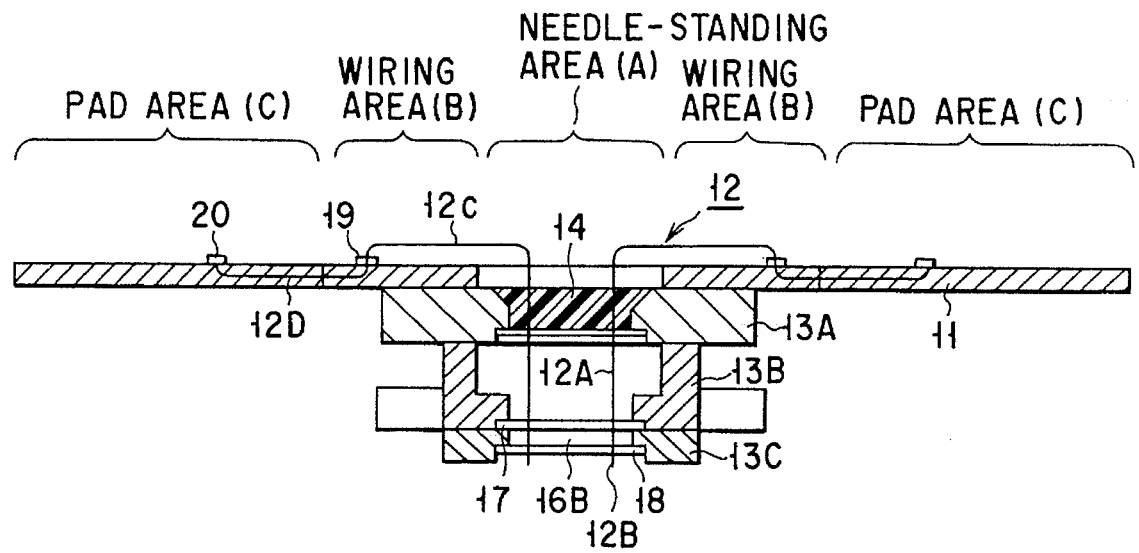
FIG. 2 is a cross-sectional view showing a structure of a probe card used in the apparatus shown in FIG. 1.

Preferred embodiments of the present invention will now be described with reference to the accompanying drawings.

For bettering the understanding of the present invention, the structure and operation of the entire probe apparatus will first be described by referring to FIG. 1.

In FIG. 1, a main stage 101 is provided at a substantially center area of a probe apparatus 100. A table 103 for fixedly supporting a semiconductor wafer 102 is attached to the main stage 101. The table 103 comprises a Z- and θ-directional stage 103A, an X-directional stage 103B and a Y-directional stage 103C. The table 103 is movable on the main stage 101 in a desired direction. A probe card assembly 104 (described later) is situated above the table 103 so as to face the semiconductor wafer 102. Although not shown, an alignment unit is provided in front of a center part of the probe apparatus 100. The alignment unit is provided with a camera or the like as an image recognition device for alignment. When an alignment step is performed, the table 103 is moved to a location below the camera.

An auto-loader 105 for loading/unloading the semiconductor wafer 102 is situated on the right-hand side (in FIG. 1) of the probe apparatus 100. An exchanger 106 for exchanging a probe card assembly 104 is situated on the left-hand side (in FIG. 1).

In the auto-loader 105, a wafer cassette 107 containing many semiconductor wafers 102 arranged at regular vertical intervals is exchangeably placed on a cassette table 108. A horizontally movable loader stage 109 and a wafer handling arm 110, which can be driven by a Y-directional driving mechanism and a Z-directional elevating mechanism (both not shown), are arranged between the wafer cassette 107 and the table 103.

When the semiconductor wafer 102 is tested by the probe card assembly 104, the wafer 102 is moved by the loader stage 109 to the vicinity of the table 103, and the wafer 102 is fixedly placed on the table 103 by the handling arm 110. Thereafter, probes (described later) of the probe card assembly 104 situated at a predetermined position are put in contact with predetermined contact points on the semiconductor wafer. Test results are transmitted to a tester 60 via a pogo pin ring 50 (described later), and the tester 60 determines the good/bad condition of the object. After the test, the semiconductor wafer 102 is restored to the loader stage 109 by the handling arm 110, and the wafer 102 is transferred to the wafer cassette 107 by the loader stage 109.

In the exchanger 106, a plurality of probe card assemblies 104, each having a probe card 10 mounted on a probe card holder 30, are placed on shelves 111 within a storage chamber 110 at predetermined vertical intervals. Each of the probe card assemblies 104 can be exchanged with the probe card assembly 104 employed within the body of probe apparatus 100 on an as-needed basis.

A monitor 112 such as a microscope or a TV camera may be provided on the tester 60 situated on the probe apparatus 100, where necessary. In this case, the monitor 112 can monitor the semiconductor wafer located below and the tip portions of the probe needles of the probe card 10 via the probe card 10 and an opening formed at a center area of the probe card holder 30. According to another practicable method of monitoring the probes, a camera facing upward may be provided on the table supporting the object for aligning the object.

Now referring to FIGS. 2, 3 and 4, the structure of the probe card 10 for probe-testing the object will be described.

The probe card 10 comprises a substantially disk-like printed board 11, probes 12 and a guide portion 13 for guiding the probes 12 to the object to be tested. The probes 12 are made of an electrically conductive material such as gold (Au) or tungsten (W). As is shown in FIG. 2, a portion 12A of the probe 12 is situated vertical to the object. At the time of the test, the table supporting the semiconductor wafer to be tested is slight moved horizontally, and thereby a tip portion 2B of the probe 12 scratches an oxide film on the semiconductor wafer surface and comes in contact with a predetermined contact point P. A portion 12C of the probe 12 projects from the upper surface of the printed board 11 and is bent substantially in parallel to the upper surface of the printed board towards the outer peripheral portion of the printed board. At point 19, the portion 12C of the probe 12 is buried in the printed board 11 and connected to a land 20 for pogo contact (described later). In the example as illustrated, a portion 12D of probe 12 is buried in the probe card 10. However, wiring may be formed on the bottom surface of the probe card 10 for easier work.

A guide portion 13, provided on the bottom surface of the printed board 11 of the probe card 10, for guiding the probes 12 comprises an upper block 13A, an intermediate block 13B and a lower block 13C. A probe fixing resin member 14 is situated at a center area of the upper block 13A. A probe fixing plate 15 is attached on the lower surface of the resin member 14. The plate 15 is provided with holes corresponding to the probes, and the probes are positioned and fixed by the holes.

Figures 3A, 3B:
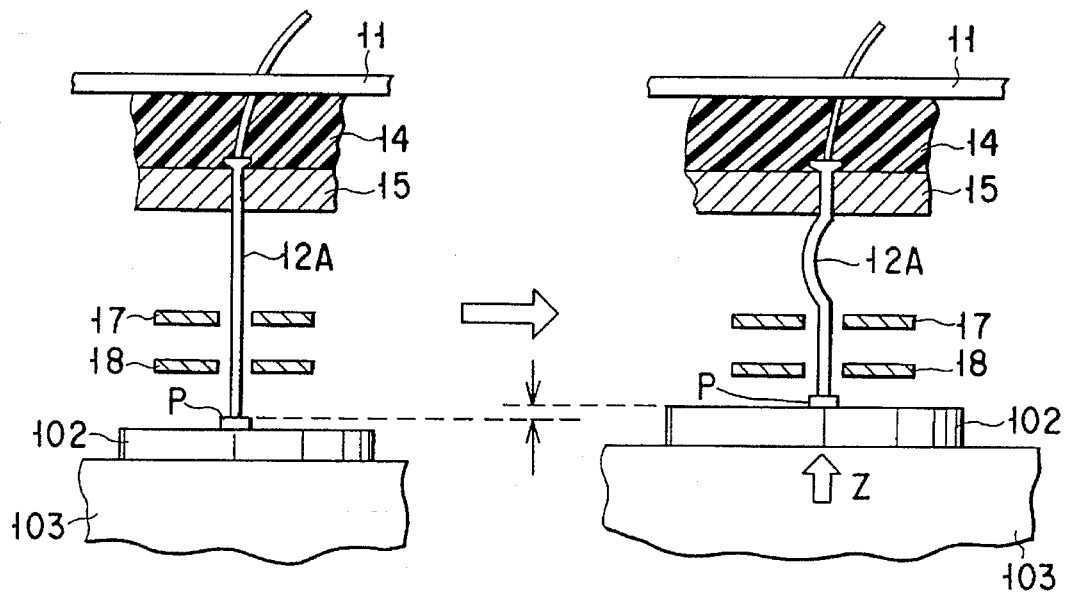
FIG. 3A is an enlarged cross-sectional view showing the state in which a tip of a probe of the probe card shown in FIG. 2 is put in contact with an object to be tested.
FIG. 3B is an enlarged cross-sectional view showing the state in which the object is raised from the state shown in FIG. 3A.

A cavity portion 16A is formed at a center region of the intermediate block 13B, and an upper guide plate 17 is attached at a lower end portion of the cavity portion 16A. The upper guide plate 17 is also provided with holes corresponding to the probe needles, and the needles are positioned and fixed by these holes. As is shown in FIG. 3B, a portion of the probe, which is located in the cavity portion 16A between the probe fixing plate 15 and the upper guide plate 17, is elastically bent as the tip portion 12B of the probe is pushed and raised vertically by an object 102 such as a semiconductor wafer.

A cavity portion 16B is also provided at a center region of the lower block 13C, and a lower guide plate 18 is attached at a lower end portion of the cavity portion 16B. The lower guide plate 18 is provided with holes corresponding to the probes, and the probes are positioned and fixed by these holes. The probes 12 are guided by the guide plates 17 and 18, and their tip portions 12B are vertically movable. FIG. 3A shows the state before the tip portion 12B of the probe is pushed by the object 102 (e.g., semiconductor wafer), and FIG. 3B shows the state after the tip portion 12B is pushed up and while being guided by the guide plates 17 and 18.

Figure 4:
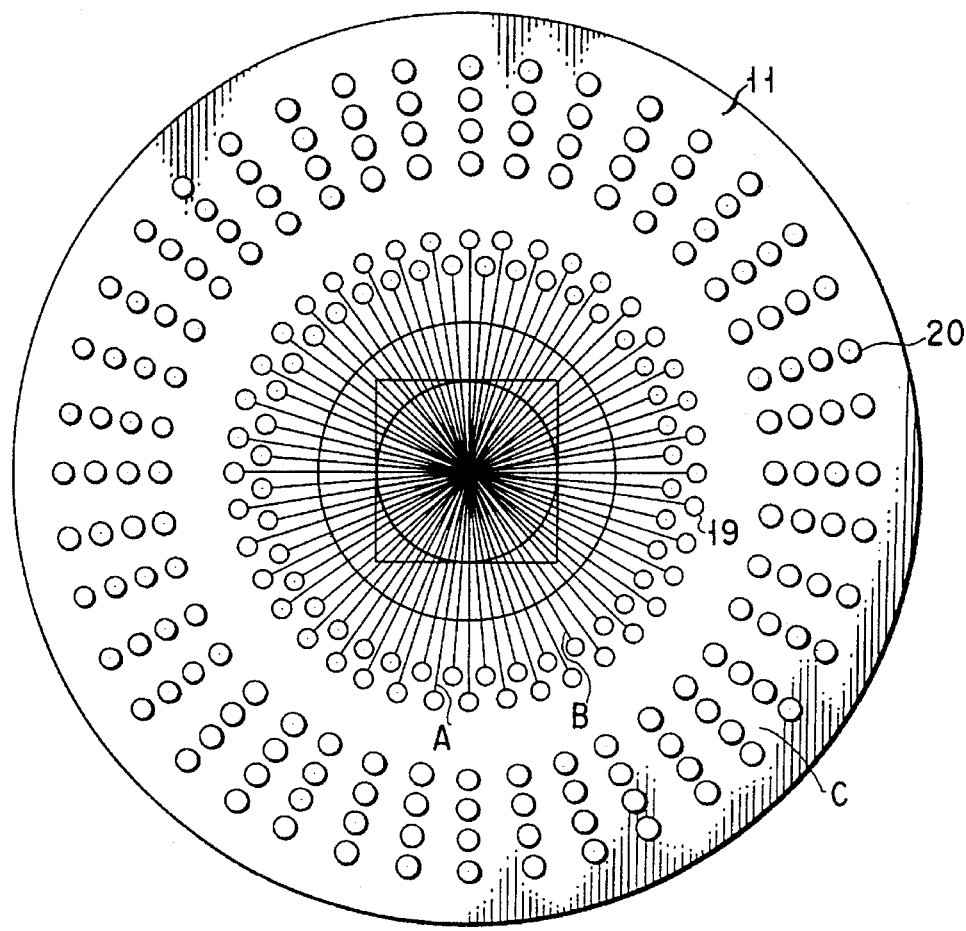
FIG. 4 is a plan view of the probe card shown in FIG. 2.

FIG. 4 is a plan view of the probe card 10 having the above structure. In the case where the integration density of semiconductor devices is increased as in chips of logic circuits and high-integration ASIC or CPU chips or supercomputers, or where simultaneous contact of two or more 16M-DRAM chips is required, the probe card is provided with many (e.g. several thousand) probe needles 12. Thus, a probe-standing area (A), a wiring area (B) and a pad area (C) are very closely arranged on the surface region of the probe card 10 in a concentric manner around an opening region 21. In the probe-standing area (A) the probe needles 12 are standed substantially perpendicularly to the semiconductor wafer. In the wiring area (B) the portions 12C of probe needles 12 are extended. In the pad area (C) the lands 20 for pogo contact are arranged. Therefore, in the currently available probe card 10, it is difficult to physically provide a space for arranging a memory device for memorizing data peculiar to the card. Furthermore, measurement signals transmitted through the densely arranged probes are vulnerable to noise other than signal components, and it is desirable that the memory device be situated away from signal lines for communication between probe apparatuses as much as possible.

In particular, in a logic circuit or a 16M-DRAM or a higher-capacity memory, an operation voltage has been lowered from conventional 5 V to, e.g. 2.4 V or less, and the threshold level has been decreased more and more. Thus, effective countermeasures to noise have been demanded in the test of the objects on which such circuits and devices are arranged.

Figure 5:
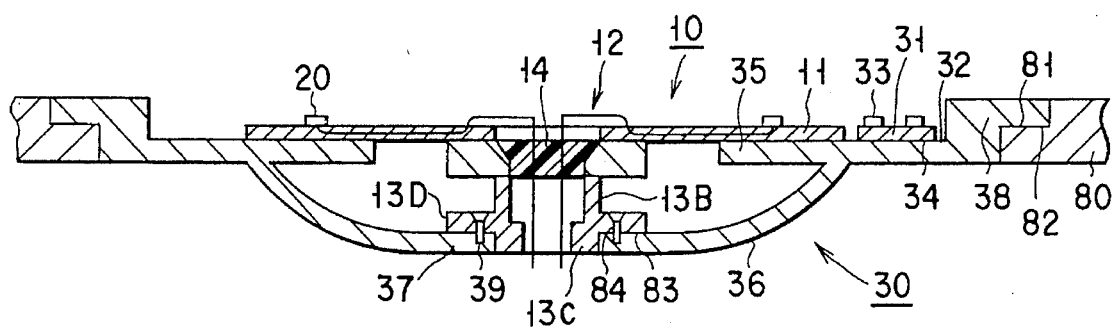
FIG. 5 is a cross-sectional view showing an example of a probe card holder used in the probe apparatus according to the present invention.
Figure 6:
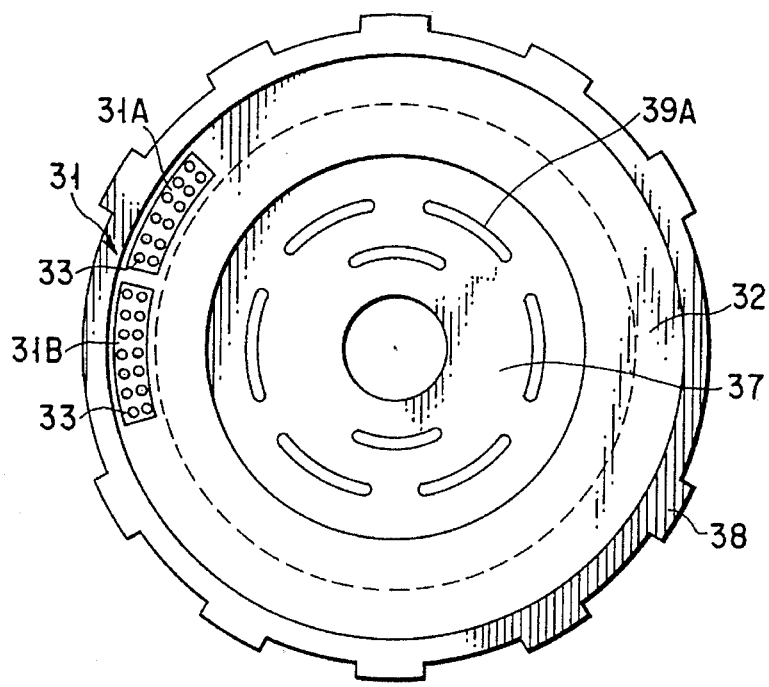
FIG. 6 is a plan view of the probe card holder shown in FIG. 5.

In the present invention, as shown in FIGS. 5 and 6, a memory device 31 for memorizing data peculiar to the probe card is provided on an area 32 on the probe card holder 30, thereby solving the above problem. By situating the memory device 31 on an area other than the probe card 10, the above problem of physical restriction can be solved, and the memory device 31 can be protected against the noise produced from the probe card 10. Moreover, the measurement signals associated with the object to be tested can be protected. Even when the probe card 10 malfunctions, there is no need to dispose of the usable memory device 31 together, unlike the prior art. As a result, the memory device 31 can be used once again. Since the probe card holder is moved along with the probe card, it is advantageous that the memory device for memorizing the data peculiar to the probe card is provided on the probe card holder.

The memory device 31 is fixed on the area 32 with a suitable insulating member 34 interposed. By providing the insulating member 34, the memory device 31 can be electrically insulated and protected from the probe card holder 30 which is normally made of a metallic material such as aluminum or stainless steel. Since the probe card holder 30 is formed of a rigid metallic material such as aluminum or stainless steel, as mentioned above, it is possible to decrease deformation or strain of the probe card due to a stress produced by contact between the tip portions of the probes and the object to be tested.

As is shown in FIG. 6, the memory device 31 comprises, for example, two memory elements 31A and 31B. Preferably, a plurality of EEPROMs (Electrically Erasable Programmable Read Only Memory) corresponding to the amount of data to be stored are used as memory data writable/readable elements. For example, one of the ROMs, 31A, stores various data relating to the probe card fixed on the probe card holder 30, which data is set before the test. The other ROM 31B stores various data relating to the probe card 10, which is rewritten each time a test is conducted.

Examples of the data items to be stored are:

(1) the height of tips of probes of the probe card from the top surface of testing object;

(2) the number of times of contact between the probe card and objects;

(3) the amount of movement between the probe card and the object in the Z-direction for over-driving;

(4) the kind and type of the probe card;

(5) the kind, type and number of elements on the object to be tested;

(6) the position of elements of the object on the object;

(7) the timing for performing probe tips polishing and the number of times of polishing;

(8) the amount of angular adjustment in the θ-direction when the probe card is transferred and placed on the probe apparatus; and (9) the history (time of exchange) of use of the probe card.

Specifically, in addition to the Z-directional movement data for controlling Z-directional movement of the table 103, there are data items: the number of times of contact (total and trip); the relative positions of probes; the serial numbers of probe cards; the kind of the probe card; the number of pins; the multi-number; the multi-location; the timing for performing probe polishing and the number of times of contact; the overdrive tolerance; the execution of slide after contact; the execution of probe polishing; and the alarm and rejection of defective probe cards.

A suitable number of pogo contact lands 33 (described later) are arranged on the upper surface of the memory device 31. A terminal (described later) having pogo pins corresponding to the lands 33 are put in pressure contact with the lands 33, thereby achieving electrical pogo contacts.

Figure 7:
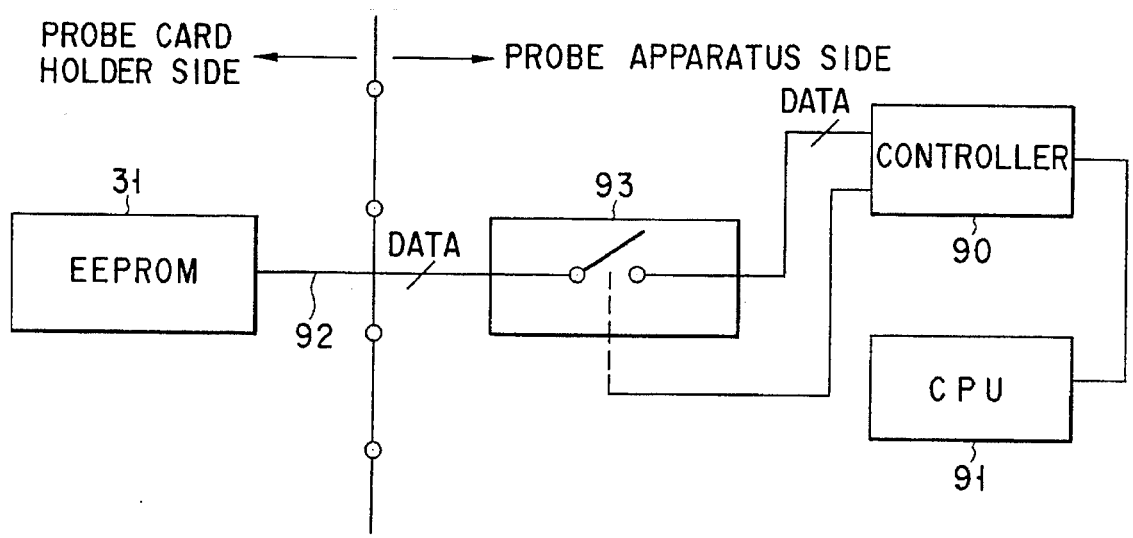
FIG. 7 is a circuit diagram illustrating the connection and flow of signals between a memory device (EEPROM) mounted on the probe card holder according to the present invention and the probe apparatus.

FIG. 7 is a block diagram showing the data transmission/reception in this case. The memory device 31, for example, EEPROM is connected to a controller 90, and data transmission/reception is effected therebetween. The controller 90 is connected to a CPU 91, and the test operation is controlled on the basis of a command from the CPU 91. The memory device 31 is connected to the controller 90 by a power supply line 92 for signals and potential of +5 V (actually plural lines are used). A relay mechanism 93 for turning on/off signals is provided along the line 92. When the memory device 31 is not accessed, the relay mechanism 93 can be turned off to prevent noise from mixing in signals of the probe card. The relay mechanism 93 may be a mechanical relay device or a relay circuit comprising transistors, etc. The relay mechanism 93 functions this way, but it is not indispensable.

The structure of the probe card holder 30 will now be described with reference to FIGS. 5 and 6. According to an embodiment of the invention, the probe card holder 30 has a disk-like shape and comprises a support portion 35, a cup-like portion 36, and an outer portion 32. The support portion 35 supports, from the bottom, a peripheral area of the probe card 10 or, preferably, the pad area (C) shown in FIG. 2 (on which the pogo contact lands 20 are arranged and a load due to the pogo pin ring, described later, is applied at the time of test). The cup-like portion 36 is curved downwards from its portion at the outer periphery of the probe card 10 towards its center portion, and the cup-like portion 36 supports the guide portion 13 of the probe card 10. The outer portion 32 is continuous with an outside portion of the support portion 35 and supports the memory device 31.

The printed board 11 of the probe card 10 is fixed on the support portion 35 by a suitable fixing member (not shown), e.g. screws.

The above-mentioned memory device 31 (comprising elements 31A and 31B) is provided on the outer portion 32. The flatness of the upper surface of the support portion 35 and the upper surface of the outer portion 32 is adjusted such that the level line of the upper surface of the pogo contact land 20 on the probe card 20 and the level line of the upper surface of the pogo contact land 33 on the memory device 31 are located in substantially the same plane. By this structure, when the pogo pin ring 50 and terminal 70 (see FIG. 10) are moved downwards, as will be described later, the probe card 10 is put in electrical contact with the pogo pin ring 50 and the terminal 70 is put in electrical contact with the memory device 31 by a single operation.

In this case, since the stress applied to the probe card 10 by the pogo pin ring 50 can be absorbed by the area 35 of the probe card holder 30, the strain of the probe card 10 due to stress can be decreased. As a result, even if the tip portions 12B of the probes requires parallelism of about ±10μm, the tip portion 12B of the probes 12 can be put in contact with the surface of the semiconductor wafer 102 with sufficiently high parallelism and uniform pressure. Thus, the precise probe test can be performed.

The bottom surface of a bottom portion 37 of the cup-like portion 36 is flush with the bottom surface of the lower block 13C of the guide portion 13. An outwardly projecting portion 13D is formed on the periphery of the intermediate block 13B of the guide portion 13. The projecting portion 13D is engaged with the bottom portion 37 of the cup-like portion 36 of the probe card holder 30, and both are fixed by fixing members 39 such as screws. By virtue of this structure, when the pogo pin ring 50 is moved downward at the time of the test, the bottom portion 37 of the cup-like portion 36 can receive the stress applied to the center portion of the probe card 10. Since the probe card holder 30 supports the probe card 10 at both the support portion 35 and cup-like portion 36, deformation of the probe card 10 due to the stress applied by the pogo pin ring 50 can be prevented.

A plurality of shoulders 38 are formed on the outer periphery of the outer portion 32. When the probe apparatus is operated, the shoulders 38 are engaged with a top plate 80 provided at an upper part of the frame of the probe apparatus 100. Thereby, the probe card holder 30 is positioned and fixedly supported on the top plate 80. By these support portions, too, the stress applied by the pogo pin ring 50 can be received.

At the time of measurement, the probe card holder 30 is mounted on the top plate 80 provided at the upper part of the frame of the probe apparatus 100. In this case, an engagement surface 81 of the shoulder portion 38 of the probe card holder 30 and an engagement surface 82 of the top plate 80 are polished and flattened with high precision and high parallelism is maintained therebetween. In addition, an engagement surface 83 of the bottom portion 37 of the cup-like portion 36 of the probe card holder 30 and an engagement surface 84 of the projecting portion 13B are also polished and flattened with high precision and high parallelism is maintained therebetween. Only by achieving high parallelism between the engagement surfaces 81 and 82 and between the engagement surfaces 83 and 84, the tip portions 12B of the probes 12 can be aligned with the object to be tested with uniform pressure and with high parallelism. Accordingly, a surface polishing process for other parts can be omitted, and the number of manufacturing steps can be reduced. Furthermore, by controlling the parallelism, the high parallelism of the tip portions 12B of the probes 12 can be maintained even if the printed board 11 of the probe card 10 is deformed.

The table 103 may include a heater. For example, the semiconductor wafer 102 is heated by the heater up to 60° C. to 150° C., and electrical characteristics of the IC chips on the wafer 102 are measured under the high-temperature condition. In other cases, cold water may be circulated in the table 103 to cool the semiconductor wafer to −10° C., and the electrical characteristics are measured. In these cases, the probe card 10 and probe card holder 30 are thermally expanded or contracted by heat radiation from the wafer or heat conduction through the tips of the needles. In particular, stress concentration due to thermal expansion or contraction occurs in the probe card holder 30 made of aluminum or stainless steel having high heat conductivity. Consequently, the probe card holder 30 itself is thermally deformed. When such thermal deformation has occurred, the balance in parallelism of the tip portions 12B of the probes is lost, and over-drive, whose amount was set at normal temperature, cannot be applied, and exact measurement cannot be effected.

By contrast, in the example shown in FIG. 6, holes or grooves 39A are formed in the cup-like portion 36 of the probe card holder 30 in the circumferential direction. Thereby, stress concentration due to thermal expansion or thermal contraction can be absorbed as elastic deformation in the holes or grooves. As a result, thermal displacement of the probe card holder 30 is reduced, and the amount of Z-directional thermal deformation of the probes 12 of the probe card 10 can be reduced. Thus, a predetermined amount of over-drive can be maintained, and the probes 12 can be put in contact with the object. Exact probe tests can be performed.

In the example shown in FIG. 6, the holes or grooves are formed in the probe card holder 30, thereby relaxing stress concentration. According to another method for relaxing stress concentration, the probe card holder 30 may be formed of a combination of materials with different thermal expansion coefficients so as to cancel thermal displacement caused in the probe card holder 30. For example, the probe card holder 30 is constructed in a multi-layer structure. A material with a high thermal expansion coefficient is employed in an upper layer of the multi-layer structure in the circumferential direction, and thereby a bimetallic effect is obtained and the probe card holder 30 is deformed to cancel the stress concentration due to heat conduction.

Figure 8:
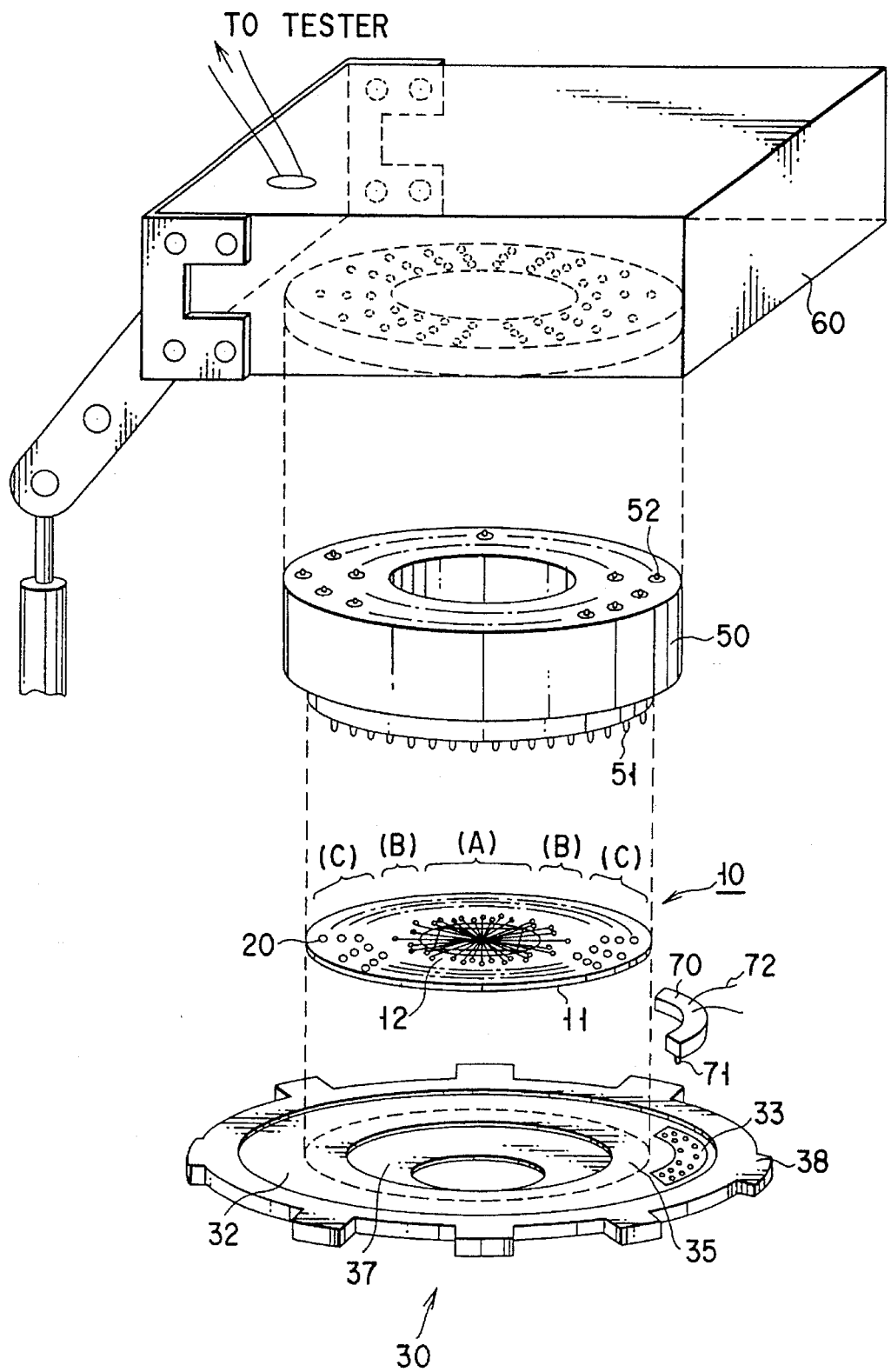
FIG. 8 is an exploded view showing the probe card holder, probe card, and pogo pin ring according to the embodiment of the present invention.
Figure 9:
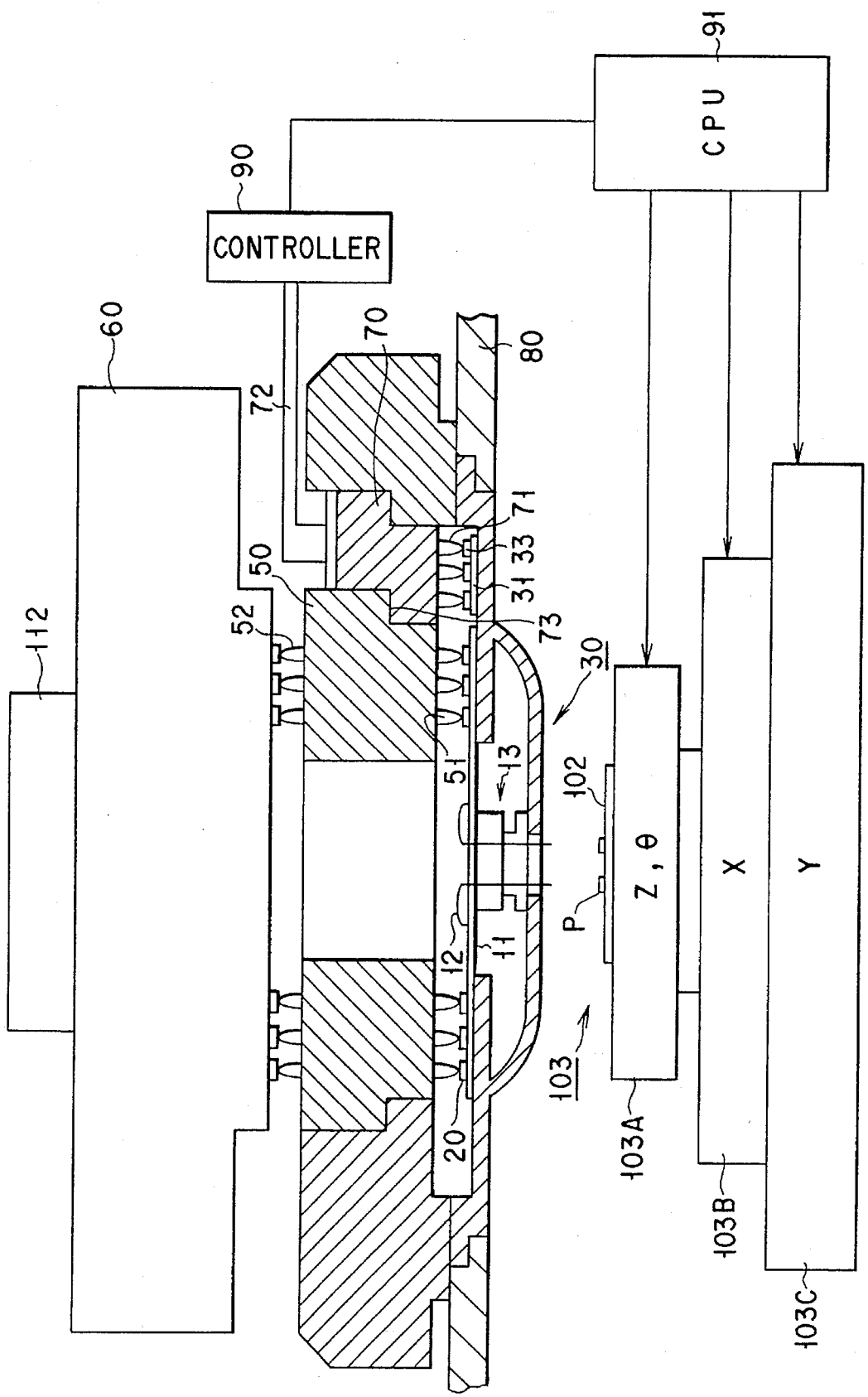
FIG. 9 shows schematically the state in which the probe card holder according to the embodiment of the present invention is mounted on the probe apparatus.

Referring to FIGS. 8 and 9, the operational state of the probe apparatus will now be described. As is shown in the exploded view of FIG. 8, the probe card 10 is placed and fixed on the support portion 35 of the probe card holder 30. At the same time, the memory device 31 is placed and fixed on the outer portion 32. At the time of the test, the pogo pin ring 50 is pressed on the probe card 10.

Figure 10:
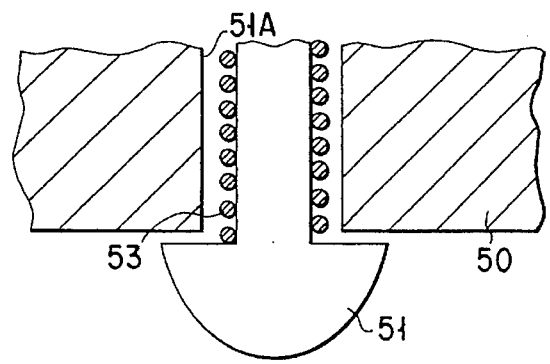
FIG. 10 is a cross-sectional view illustrating the pogo pin.

As is shown in FIGS. 8 and 9, the pogo pin ring 50 is a substantially cylindrical member having a cylindrical space in its center portion. The lower surface of the pogo pin ring 50 is provided with pogo pins 51 corresponding to the lands 20 arranged appropriately on the pad area C of the probe card 10. As is shown in FIG. 10, a pogo pin 51 is urged downwards by a coil spring 53 situated within a pin insertion hole 51A.

At the time of the test, the pogo pin ring 50 is moved downwards by suitable driving means, and the pogo pins 51 come into pressure contact with the lands 20 of the probe card 10. Thus, test data is transmitted from the probes 12 via the pogo pins. The upper surface of the pogo pin ring 50 is also provided with pogo pins 52. At the time of the test, the pogo pins 52 are brought into electrical contact with the corresponding lands of the tester 60. The test data from the probes is transmitted to the tester, and the tester 60 determines the good or bad condition of the object.

A terminal 70 is connected to the memory device 31. The lower surface of the terminal 70 is provided with pogo pins 71, and these pogo pins 71 are put in contact with the lands 33 on the memory device 31. Predetermined data is transmitted to the controller 90 via cables 72.

The controller 90 is connected to the CPU 91. The CPU 91 delivers necessary driving signals to the table 103 on the basis of signals from the controller 90, thereby optimally driving the stages 103A, 103B and 103C.

As is shown in FIG. 9, the pogo pin ring 50 and the terminal 70 are engaged with each other at mutually facing surfaces 73, and the lands 20 of the probe card 10 and the lands 33 of the memory device 31 are adjusted to be situated in substantially the same plane. Thus, the pogo pins 51 and 71 can be put in contact with the lands 20 of probe card 10 and the lands 33 of memory device 31 by a single operation.

Other embodiments of the probe card holder will now be described.

Figure 11:
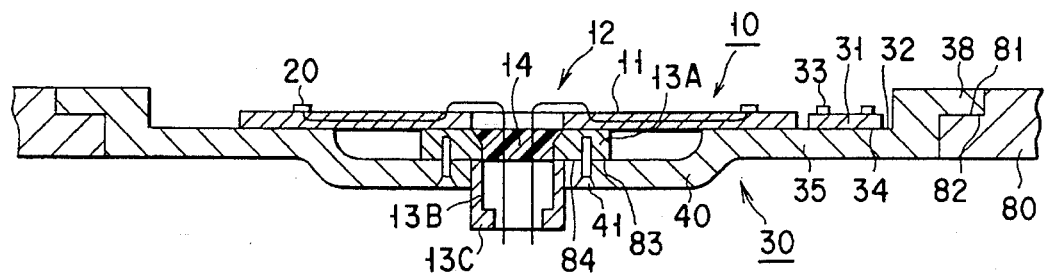
FIG. 11 is a cross-sectional view showing a probe card holder of another example.

A probe card holder in FIG. 11 differs from that of FIG. 5 in that the cup-like portion 36 curving downwards from the peripheral portion of the probe card 10 is replaced with a cup-like portion 40 curving downwards from an end portion of the support portion 35, i.e. a boundary portion between the wiring area (B) and the pad area (C). The cup-like portion 40 is engaged with the lower surface of the upper block 13A of the guide portion 13 and fixed by fixing members 41 such as screws. As a result, the cup-like portion 40 receives the stress applied to the center portion of the probe card 10 when the pogo pin ring 50 is moved downwards, and the occurrence of strain of the probe card 10 due to the stress can be prevented.

Figure 12:
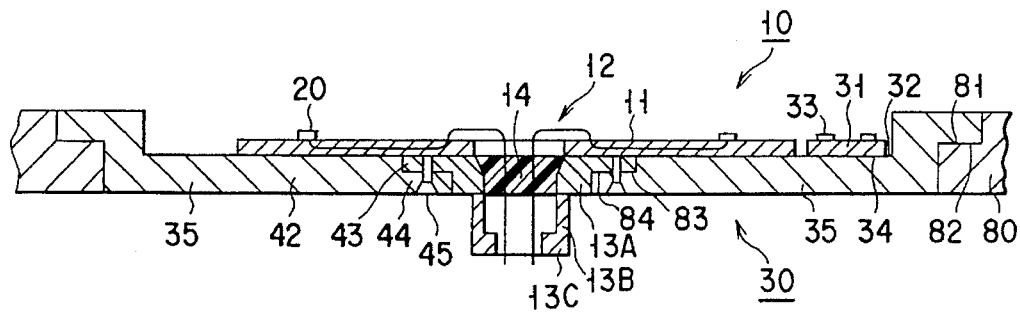
FIG. 12 is a cross-sectional view showing a probe card holder of still another example.

In a probe card holder shown in FIG. 12, the structure thereof is simplified. In the holder of FIG. 12, the support portion 35 of the probe card holder 30 extends substantially straight from the pad area (C) to an area 42 and supports the wiring area (B) of the probe card 10, too. Further, a shoulder portion 43 is formed on the outer periphery of the upper block 13A of the guide portion 13 of the probe card 10. The lower face of the shoulder 43 is engaged with an engaging portion 44 of the probe card holder 30 and fixed by fixing members 45 such as screws. Since almost the entire area of the probe card 10 is supported by the probe card holder 30, stress concentration does not occur and the occurrence of strain of the probe card 10 due to stress is prevented.

Figure 13:
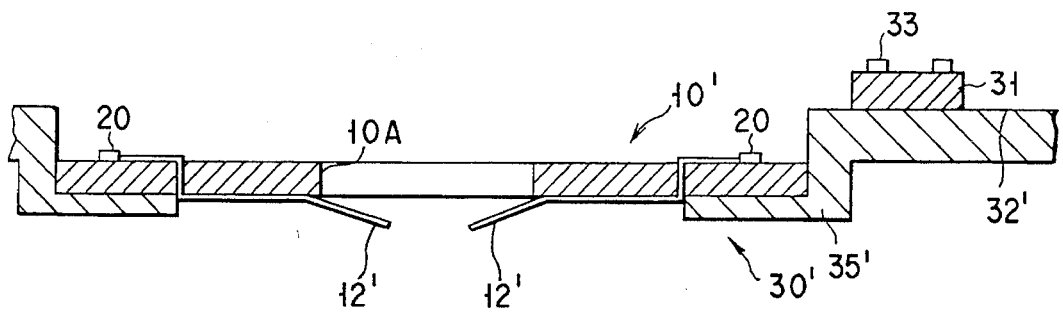
FIG. 13 is a cross-sectional view showing a probe card of another example.

In the above description, so-called vertical probe type probe cards wherein probes are standed perpendicularly to the object have been illustrated. However, the present invention is not limited to these probe cards. For example, this invention is applicable to a conventional probe apparatus employing so-called lateral probe type probe cards wherein tungsten probes inclined to the object are arranged on the upper or lower surface of the card and tip portions of the probes are put in contact with the object, as shown in FIG. 13. In a lateral probe type probe card 10', tungsten probes 12' extend from lands 20 and tip portions of the probes 12' are situated below a hole formed at a center portion of the card 10'. The probe card holder 30' includes a support portion 35' for supporting the probe card and an outer portion 32' which is situated outside the support portion 35' and supports the memory device 31.

Furthermore, this invention is applicable to a rubber type probe card using an electrically conductive rubber contact, a membrane type probe card using a bump film, and holders thereof.

As has been described above, according to the probe apparatus of the present invention, even if the number of probes is increased and the physical space on the surface of each probe card is insufficient, the peculiar data necessary for measurement of the cards can be stored and managed in the memory device situated on the probe card holder. Since the memory device is situated on the holder which is away from the signal lines of the probe card, the measurement signals can be protected against noise or cross-talk between the high-speed signal lines of the probe card and the data control lines of the memory device. Moreover, if a tip portion of the probe of the probe card is worn or damaged, only the probe card is exchanged and the probe card holder is used once again.

According to the probe apparatus of the present invention, when a pressing force is applied to the probe card from the pogo pin ring at the time of measurement, the two parts of the probe card holder receives the load applied to the probe card. Thus, non-uniform stress is prevented from being applied to the probe card, and deformation or strain of the probe card can be prevented.

According to the structure of this invention, in the case where the object is measured at high temperatures or low temperatures, thermal deformation of the probe card holder itself can be decreased. Thus, the contact between the tip portion of the needle and the object is maintained at optimal pressure and exact measurement can be performed.

Furthermore, since the parallelism and pressure at the tip portion of the probe needle can be maintained uniformly, high-precision probe tests can be performed.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A probe apparatus for measuring electrical characteristics of an object to be tested by putting a plurality of probes in electrical contact with the object, said apparatus comprising:

an apparatus body;

probe card means having a plurality of probes, a base plate for supporting said probes, and a guide member for guiding said probes, said guide member extending to a region near tip portions of the plurality of probes; and a probe card holder for holding said probe card means at a measurement position facing said object within the apparatus body, wherein said probe card holder includes a first portion for supporting an outer peripheral portion of a lower surface of the base plate of said probe card means and a second portion engaged with said guide member of the probe card means, said second portion connecting said first portion and said guide member, with said second portion engaged with said guide member at said region near a tip portion of the plurality of probes, said probe card holder preventing said base plate from being deformed and holding the base plate substantially flat.

2. The apparatus according to claim 1, wherein said guide member guides said probes perpendicularly to said object and said probes bend between said base plate and said object when said probes are pushed by said object.

3. The apparatus according to claim 1, wherein said probe card holder includes a third portion outside said first portion, and memory means for memorizing data for measuring the object by using said probe card means is provided on a surface portion of said third portion.

4. The apparatus according to claim 3, wherein said memory means includes an electrically erasable programmable read only memory capable of reading and writing data.

5. The apparatus according to claim 3, wherein said probe card holder is made of an electric conductive material, said memory means includes a memory device and insulating means is interposed between said third portion of the probe card holder and said memory device.

6. The apparatus according to claim 1, further comprising contact means for transmitting test data obtained through measurement by said probe card means to a tester, wherein said probe card means is held between said contact means and said probe card holder at the time of measurement.

7. The apparatus according to claim 6, wherein said contact means includes a connection pin and a spring member for urging said connection pin to a connection portion.

8. The apparatus according to claim 1, wherein said guide member is formed in a central portion of said base plate and guides said probes perpendicularly to said object.

9. The apparatus according to claim 1, wherein said first portion of said probe card holder is plate-like, and said second portion is cup-like.

10. The apparatus according to claim 1, wherein said first portion of said probe card holder is flat, and said second portion is curved, said second portion extending from said first portion to said guide member.

11. The apparatus according to claim 1, wherein said first portion includes a flat surface disposed above said guide member and said base plate is supported on said flat surface, said second portion extending downwardly and radially inwardly from said first portion to a bottom of said guide member.

* * * * *